United States Patent
Goldenstedt

(10) Patent No.: US 9,123,326 B2
(45) Date of Patent: Sep. 1, 2015

(54) ENDOSCOPIC DEVICE FOR GENERATING ACOUSTIC WAVES WITH VARIABLE FOCUS

(71) Applicant: Storz Medical AG, Tägerwilen (CH)

(72) Inventor: Cédric Goldenstedt, Tägerwilen (CH)

(73) Assignee: STORZ MEDICAL AG, Tagerwilen (CH)

( * ) Notice: Subject to any disclaimer, the term of this patent is extended or adjusted under 35 U.S.C. 154(b) by 0 days.

(21) Appl. No.: 14/075,042

(22) Filed: Nov. 8, 2013

(65) Prior Publication Data

US 2014/0126335 A1    May 8, 2014

(30) Foreign Application Priority Data

Nov. 8, 2012   (EP) ..................................... 12191867

(51) Int. Cl.
*G10K 11/35* (2006.01)
*A61N 7/02* (2006.01)
*A61N 7/00* (2006.01)

(52) U.S. Cl.
CPC .............. *G10K 11/352* (2013.01); *A61N 7/022* (2013.01); *A61N 2007/0065* (2013.01); *A61N 2007/0078* (2013.01); *A61N 2007/0082* (2013.01); *A61N 2007/0091* (2013.01)

(58) Field of Classification Search
CPC ....................................................... A61N 7/02
USPC ........................................................ 606/27
See application file for complete search history.

(56) References Cited

U.S. PATENT DOCUMENTS

| | | | |
|---|---|---|---|
| 5,676,692 A * | 10/1997 | Sanghvi et al. .................. 606/27 |
| 6,231,511 B1 * | 5/2001 | Bae .............................. 600/447 |
| 6,379,320 B1 | 4/2002 | Lafon ................................ 601/3 |
| 6,635,054 B2 * | 10/2003 | Fjield et al. ..................... 606/27 |
| 2003/0004439 A1* | 1/2003 | Pant et al. ......................... 601/2 |
| 2003/0018255 A1 | 1/2003 | Martin et al. ................. 600/437 |
| 2005/0096542 A1 | 5/2005 | Weng et al. ................... 600/439 |
| 2012/0089021 A1* | 4/2012 | Peyman ........................ 600/439 |

FOREIGN PATENT DOCUMENTS

DE          44 43 947          7/1995

OTHER PUBLICATIONS

Extended European Search Report in European Application No. 12191867.6 dated Feb. 28, 2013.

* cited by examiner

*Primary Examiner* — Michael Peffley
(74) *Attorney, Agent, or Firm* — Norton Rose Fulbright US LLP

(57) ABSTRACT

An endoscopic device for generating acoustic waves with a sheath defining a center axis contains a first transducer for generating a first beam of acoustic energy radiating outwards of the endoscope sheath and a second transducer for generating a second beam of acoustic energy radiating outwards of the endoscope sheath. Both beams have different directions and intersect outside of the endoscope forming a focus spot. The second transducer is linearly movable parallel to the center axis with respect to the first transducer to displace the second beam and therefore to displace the intersection of the beams and therefore of the focus spot.

16 Claims, 4 Drawing Sheets

ENDOSCOPIC DEVICE FOR GENERATING ACOUSTIC WAVES WITH VARIABLE FOCUS

PRIORITY CLAIM

This application claims priority to pending European Application No. 12191867.6 filed on 8, Nov. 2012.

BACKGROUND OF THE INVENTION

1. Field of the Invention

The invention relates to the ablation of pathological tissues, such as tumors, or nodules, through a precise local heating. This is done by applying physical energy radiation e.g. by acoustic waves into the targeted tissue, which is converted into heat therein. As soon as the temperature reaches a certain level of about 80° C., tissue is coagulated and a necrosis develops.

2. Description of Related Art

For a non-invasive treatment, in the U.S. Pat. No. 6,379,320 B1 a focused ultrasound source is provided in the tip of an endoscope for radiating radially. The focus spot cannot be adjusted; therefore, the endoscope must be brought close to the region to be treated, which is often not possible.

An endoscope with integrated ultrasound source is disclosed in DE 44 43 947 A1. For generating an ultrasound wave, which is focused at a variable distance, a large number of phased-array transducer elements are provided which are driven by individual oscillators. This requires complex electronics, and the power output of the transducer is limited due to acoustic crosstalk between the individual transducer elements The US patent application publication US 2003/0004439 A1 discloses and intrabody HIFU (High Intensity Focused Ultrasound) applicator, which uses a plurality of ultrasound transducers mounted on a flexible holder. These transducers are transported by an endoscope into the body, but operated outside of the endoscope. Therefore, a significant amount of space is required within the body, which severely limits the application range of this instrument

SUMMARY OF THE INVENTION

The embodiments are based on the object of providing an endoscopic HIFU ultrasound applicator, which delivers a high acoustic energy level, has an adjustable focus spot and can be kept within an endoscope In an embodiment, acoustic energy is delivered by at least two radiation emitters within an endoscope, whereby at least one radiation emitter is linearly movable relative to another radiation emitter. Both emitters are radiating under different angles into the same direction having an intersection under an intersecting angle outside the endoscope. This intersection defines the focus spot of the ultrasound applicator. By moving at least one radiation emitter, the position of the intersection and therefore the focus spot moves. To achieve a good absorption of the acoustic energy in tissue, preferably a frequency in the range between one and 10 MHz is selected. Due to the invention, the focus spot can be moved and adapted to actual requirements. It may be anywhere between the surface of the endoscope and deep within the surrounding tissue. The maximum depth that may be up to 40 mm. By means of an actuating element like a wire or even a motor or any other actuator, the focus point may be adjusted during treatment. By using a moving focus spot, a certain area of the tissue may be scanned to treat a larger volume. Such a scanning may also be done automatically or at least controlled by a control unit like a computer. Generally, the position of the focus spot may be dynamically controlled by such a control unit and adapted to a predefined and/or required area. For this purpose, the control unit may be connected to an ultrasound and/or x-ray imaging system.

Herein, generally reference is made to an endoscope. It is understood that the invention may also be applied to any kind of similar instruments like a laparoscope, a catheter, or any intraluminal or interstitial probe, which are referred herein also under the term of 'endoscope'.

Furthermore, reference is made to emitters, which may be any kind of acoustic energy sources like any kind of ultrasonic transducers, e.g. Piezo transducers, capacitive or piezoelectric micromachined ultrasound transducers (cMUTS and pMUTS), piezocomposite transducers, shockwave transducers. An emitter is an active device and is no reflector like a mirror for reflecting acoustic energy generated by a transducer, nor a deflecting element like a prism.

In a first embodiment of the invention, two emitters are provided. A first emitter preferably radiates radially outwards of the endoscope. A second emitter is linearly movable with respect to the first emitter, preferably along the center axis of the endoscope. The beams of radiation of the first emitter and the second emitter are intersecting outside of the endoscope and forming the focus spot. Preferably, the first and the second emitters are transducers.

In a second embodiment, at least one of the emitters is a reflector, while the other emitter is a transducer. Acoustic energy is generated by a transducer directed to the at least one reflector, which diverts the radiation energy outside the endoscope.

It is further preferred, if there is a cover, which most preferably is of elastic material, for closing an opening within the endoscope sheath over the emitters to allow unattenuated radiation of acoustic energy to the outside of the endoscope. It is further preferred, if an inner volume under the cover is filled with a preferably non or low-absorbing acoustic fluid.

In a further embodiment of the invention an imaging device, like ultrasound transducer, optical system or elastographic system may be provided within the endoscope.

BRIEF DESCRIPTION OF THE DRAWINGS

In the following, the invention will be described by way of example, without limitation of the general inventive concept, on examples of embodiment and with reference to the drawings.

Figure 1:
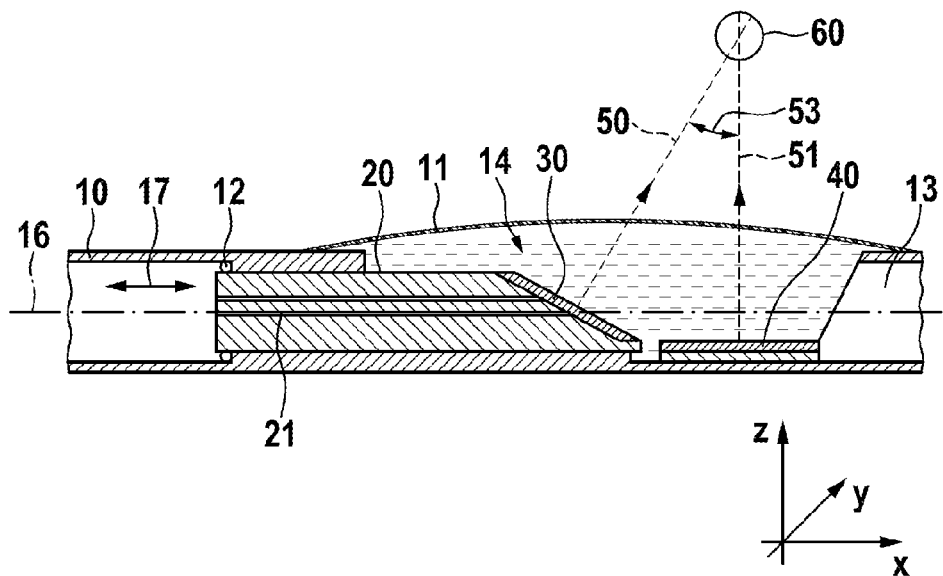
FIG. 1 shows a first embodiment of an endoscopic device for generating acoustic waves.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In FIG. 1, a first embodiment of an endoscopic device for generating acoustic waves is shown. A first transducer 40 and a second transducer 30 are contained within an endoscope sheath 10, having an opening to allow the exit of acoustic energy to an outside of the endoscope. The first transducer 40 generates a first beam 51 of acoustic energy, which preferably exits the endoscope under a predetermined angle, preferably under a right angle to the center axis 16 of the endoscope. The second transducer 30 generates a second beam 50 of acoustic energy, which preferably exits the endoscope under an angle different to the exit angle of the first transducer. The first beam 51 and the second beam 50 intersect under an intersecting angle 53 outside of the endoscope at an intersecting point 60, also referred as focus spot. Preferably, the second transducer 30 is mounted to a first slider 20, which may be moved in the direction 17 of the center axis 16 of the endoscope. The slider may contain at least one conduit 21 for liquids and/or electrical lines. There may be a cover 11 covering the opening of the endoscope sheath 10 and further enclosing an inner volume 14, which preferably is filled with an acoustic coupling fluid. Preferably there is at least one sealing 12 for sealing the inner volume at a gap of movement of the first slider 20 against the endoscope sheath 10. When moving the first slider 20, the inner volume 14 changes. Accordingly acoustic fluid must be filled in or removed, which may be done through the at least one conduit 21. The cover 11 may also be an elastic cover, which may extend or shrink, when the first slider 20 is moved.

Figure 2:
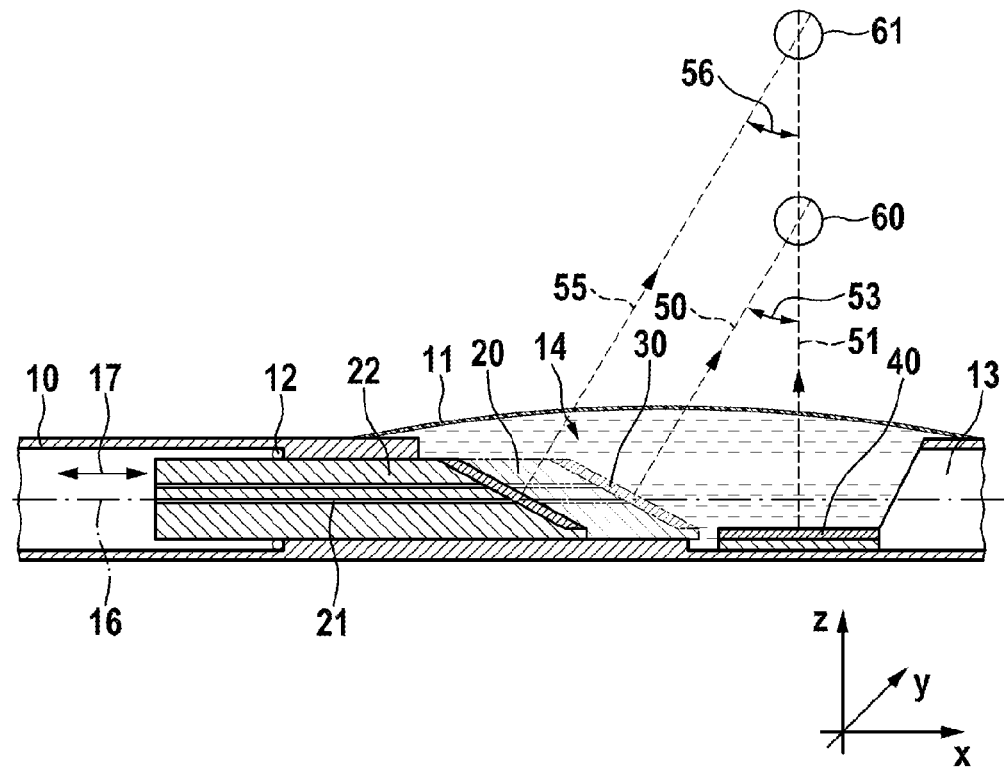
FIG. 2 shows the basic function.

In FIG. 2, the basic function of the endoscope device is shown. The first slider 20 as shown in the previous figure may be moved to second position 22, which is more distant from the first transducer 40 than the first position. From the second position, it radiates a second beam 55 of acoustic energy, basically under the same angle as from the first position. The second beam 55 is intersecting with the first beam 51 of the first transducer under a second intersecting angle 56 resulting in the second focus spot 61. As there was only a linear displacement of the second transducer, the second beam 55 from the second position is parallel to the second beam 50 from the first position. Consequently the second intersecting angle 56 is the same or approximately the same as the first intersecting angle 53. The second focus spot 61 has moved outward from the first focus spot 60. Accordingly, a linear movement of the second transducer 30 by moving the slider 20 results in a preferably radial displacement of the focus spot. The focus spot may also be moved by moving the first transducer and keeping the second transducer fixed or even by moving both transducers. When moving the first transducer, the focus spot not only moves radially, but it also moves laterally in the direction of the center axis 16.

Figure 3:
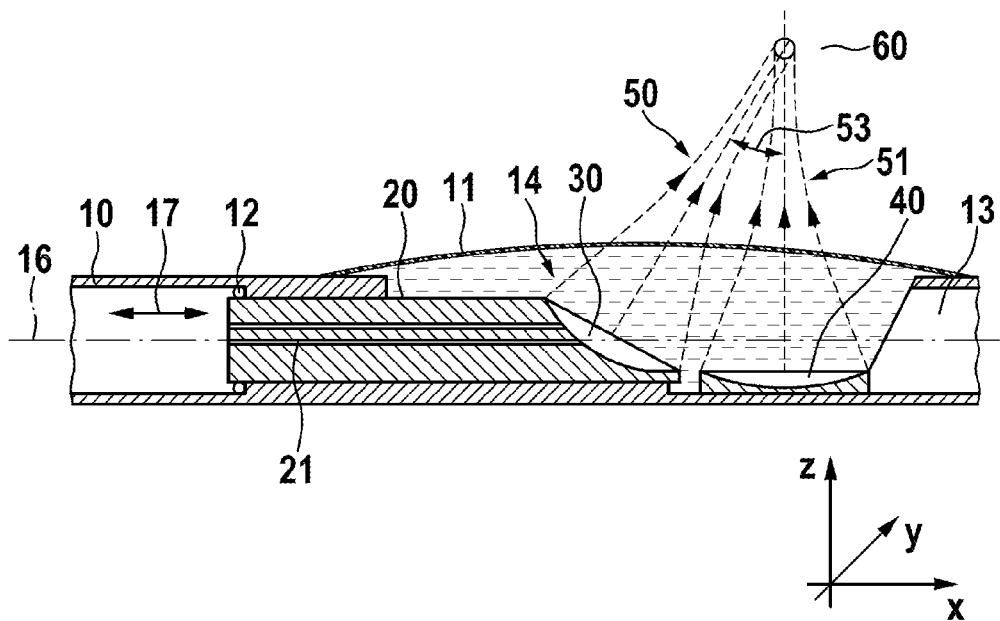
FIG. 3 shows another embodiment with modified emitters.

In FIG. 3, another embodiment with modified radiation sources is shown. Here the radiation sources 40 and 30 are focused transducers emitting narrower beams 51 and 50 resulting in a smaller focus spot 60. Here the energy density at the surface of the endoscope defined by the cover 11 is comparatively low and prevents unwanted effects like coagulation of the tissue at the surface of the endoscope.

Figure 4:
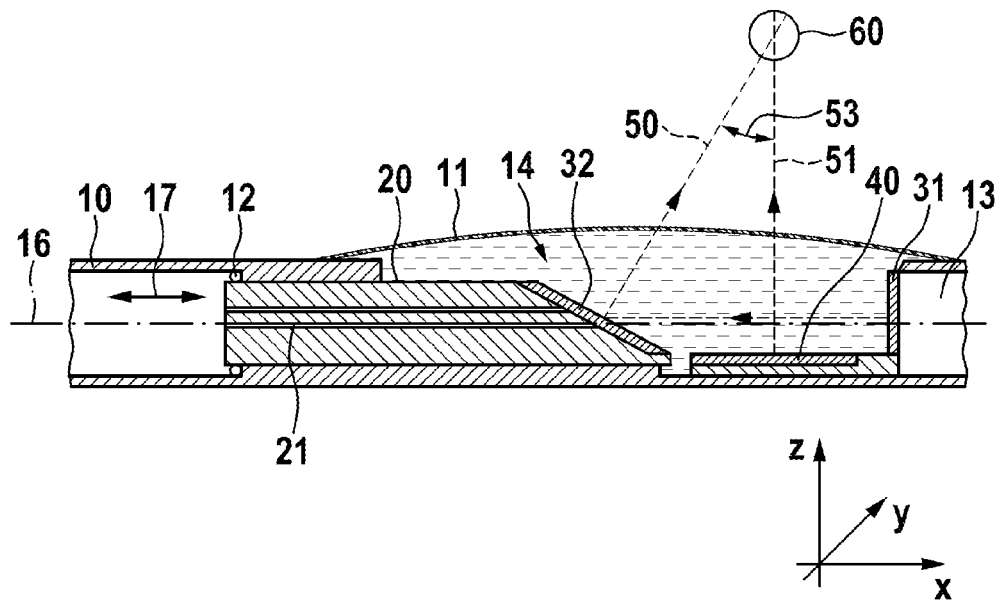
FIG. 4 shows a further embodiment with a reflector.

In FIG. 4, a further embodiment with a mirror is shown. Herein the second emitter is a reflector 32. The acoustic energy is generated by a transducer 31, which may be located in the end section 13 of the endoscope. This transducer 31 radiates acoustic energy towards the reflector 32 which itself deflects the acoustic energy into a second beam 50 to form a focus spot 60 together with a first beam 51. The basic function is the same, as if there would be a transducer 30 instead of the reflector 32.

Figure 5:
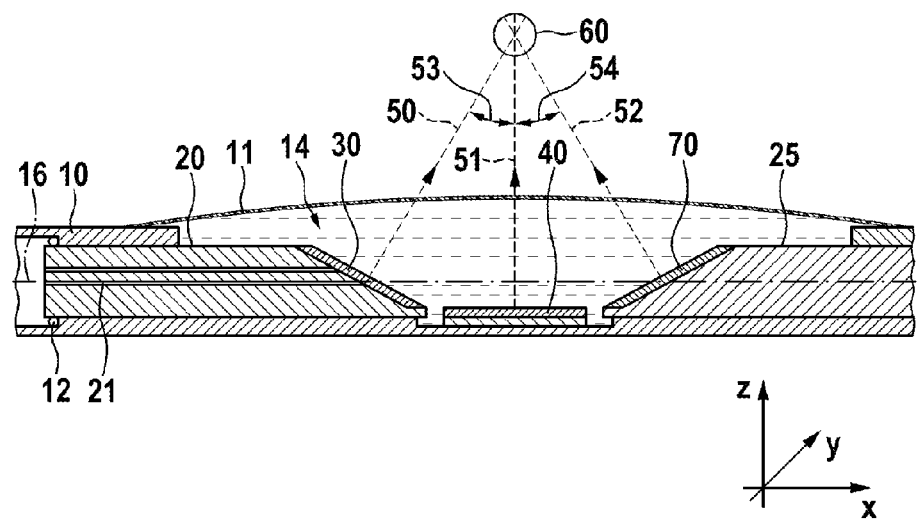
FIG. 5 shows an embodiment with two movable and one stationary emitters.

In FIG. 5, an embodiment with two movable radiation sources is shown. This embodiment is based on the previous embodiments. Furthermore, a third transducer 70 has been added. This first transducer 70 generates a third beam 52 intersecting first beam 51 under a third intersecting angle 54. The focus spot accumulates the energy of all three beams 50, 51, 52. The first transducer 70 may be supported by a second slider 25, which may also be moved parallel to the center axis 16 of the endoscope. This second slider may be moved for the same amount, but in the opposite direction of the first slider to keep a small focus spot. It may also be used independently of the first slider to form a variable and/or increased focus spot.

Figure 6:
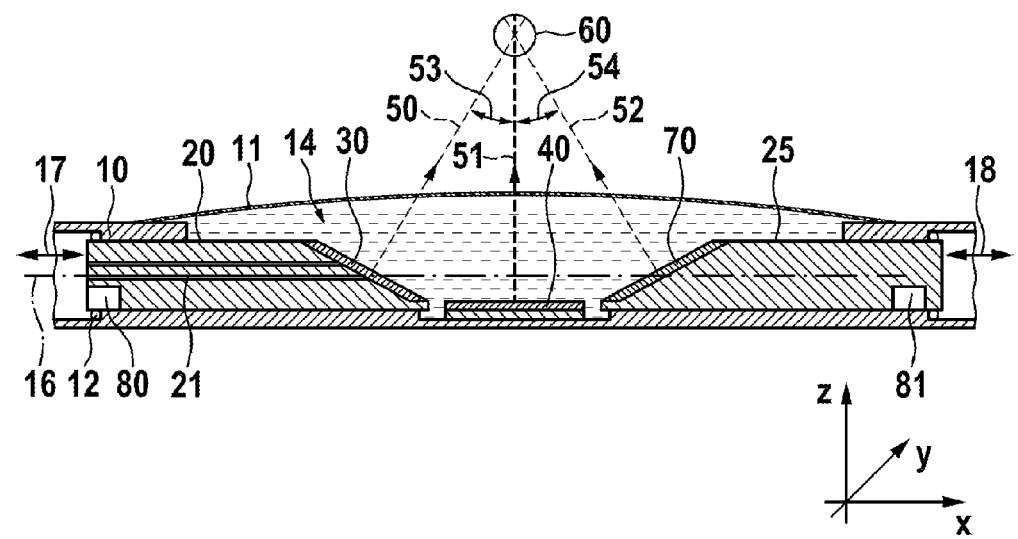
FIG. 6 shows an embodiment with two movable emitters.

In FIG. 6, a similar embodiment, but without the stationary emitter 40 is shown. This embodiment permits to adjust the position of the focus spot not only radially but also in the whole z-x plane. Here, the first slider 20 may be moved into first directions 17, preferably by a first drive means 80 and preferably parallel to the center axis 16 as shown by the arrow 17. Furthermore, the second slider 25 may be moved into second directions 18, preferably by a second drive means 81 and preferably parallel to the center axis 16 as shown by the arrow 18. Such a drive means may be a linear motor preferably having at least one coil and/or at least one permanent magnet. It may also be a drive wire, driven by an external motor or hand operated. If the first and second sliders 20 and 25 are moved in opposite directions and of the same quantity, the focus spot moves in the radial direction 63. If the first and second sliders 20 and 25 are moved in the same direction and of the same quantity, the focus spot moves laterally in the direction 62. When moving only one slider, the focus spot not only moves radially, but it also moves laterally.

Figure 7:
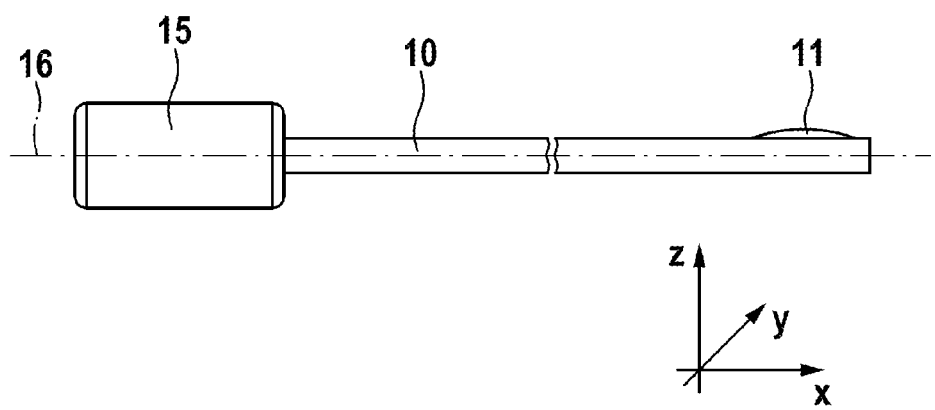
FIG. 7 shows an endoscope.

In FIG. 7, an endoscope is shown. The endoscope has a sheath 10 defining a center axis 16. There is a proximal end having a handle 15 and a distal end bearing the transducers, which are covered by a cover 11.

It will be appreciated to those skilled in the art having the benefit of this disclosure that this invention is believed to provide endoscopic devices for generating acoustic waves. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

10 endoscope sheath
11 cover
12 ceiling
13 end section
15 handle
14 inner volume
16 center axis 17 direction of movement
18 second direction of movement
20 first slider
21 conduits
22 second position of first slider
25 second slider
30 second emitter
31 transducer
32 reflector
40 first emitter
50 second beam
51 first beam
52 third beam
53 first intersecting angle
54 first intersecting angle
55 second beam from second position
56 second intersecting angle
60 focus spot
61 second focus spot
62 movement of focus spot parallel to x-axis
63 movement of focus spot parallel to y-axis
70 third emitter
80 first drive means
81 second drive means

The invention claimed is:

1. An endoscopic device for generating acoustic waves, the endoscopic device comprising an endoscope having a sheath and defining a center axis, the sheath comprising:
   a first transducer configured to generate a first beam of acoustic energy that radiates outwards of the endoscope sheath at a predetermined first angle,
   a second transducer configured to generate a second beam of acoustic energy that radiates outwards of the endoscope sheath at a second angle that is different than the first angle such that the first beam and the second beam intersect at an intersection angle outside of the endoscope to define a focus spot,
   wherein the second transducer is linearly movable parallel to the center axis with respect to the first transducer to displace the second beam and therefore to displace the intersection of the first beam and the second beam at a second intersection angle to define a displaced focus spot, and
   wherein the second intersection angle is the same as the first intersection angle.

2. An endoscopic device according to claim 1, wherein the sheath further comprises:
   a third transducer configured to generate a third beam of acoustic energy that radiates outwards of the endoscope sheath and intersects with at least the first beam outside of the endoscope.

3. An endoscopic device according to claim 2, wherein the third transducer is mounted to a second slider which is movable within the endoscope sheath.

4. An endoscopic device according to claim 3, wherein at least one second drive means is provided within the endoscope to move the second slider.

5. An endoscopic device according to claim 4, wherein the at least one second drive means is configured to perform a continuous movement for scanning a specific region of tissue surrounding the endoscope.

6. An endoscopic device according to claim 2, wherein the second and the third transducers are movable independent of each other.

7. An endoscopic device according to claim 2, wherein the second and the third transducers are movable in the same and/or opposite direction.

8. An endoscopic device according to claim 1, wherein at least one of the first and second transducers is mounted to a first slider which is movable within the endoscope sheath.

9. An endoscopic device according to claim 8, wherein at least one first drive means is provided within the endoscope to move the first slider.

10. An endoscopic device according to claim 9, wherein the at least one first drive means is configured to perform a continuous movement for scanning a specific region of tissue surrounding the endoscope.

11. An endoscopic device according to claim 1, wherein the first beam radiates radially.

12. An endoscopic device according to claim 1, wherein the first beam radiates at a right angle to the center axis of the endoscope sheath.

13. An endoscopic device according to claim 1, wherein the endoscope sheath has an opening above the transducers.

14. An endoscopic device according to claim 13, wherein the opening above the transducers is covered by a cover that encloses an inner volume.

15. An endoscopic device according to claim 13, wherein the inner volume is filled with an acoustic coupling liquid.

16. An endoscopic device for generating acoustic waves, the endoscopic device comprising an endoscope having a sheath and defining a center axis, the sheath comprising:
   a first transducer configured to generate a first beam of acoustic energy that radiates outwards of the endoscope sheath at a predetermined first angle,
   a second transducer configured to generate a second beam of acoustic energy that radiates outwards of the endoscope sheath at a second angle that is different than the first angle such that the first beam and the second beam intersect outside of the endoscope to define a focus spot,
   wherein the second transducer is linearly movable parallel to the center axis with respect to the first transducer to displace the second beam and therefore to displace the focus spot at the intersection of the first beam and the second beam without changing the second angle.

* * * * *